(12) United States Patent
Hearn et al.

(10) Patent No.: US 11,931,504 B2
(45) Date of Patent: Mar. 19, 2024

(54) INHALER PARTICULARLY A CANNABINOID INHALER AND A METHOD OF ASSEMBLING SUCH AN INHALER

(71) Applicant: SENZER LIMITED, London (GB)

(72) Inventors: Alex Hearn, London (GB); Paul Young, London (GB); Guillaume Parrin, London (GB)

(73) Assignee: SENZER LIMITED, London (GB)

( * ) Notice: Subject to any disclaimer, the term of this patent is extended or adjusted under 35 U.S.C. 154(b) by 575 days.

(21) Appl. No.: 16/754,588

(22) PCT Filed: Oct. 4, 2018

(86) PCT No.: PCT/GB2018/052830
§ 371 (c)(1),
(2) Date: Apr. 8, 2020

(87) PCT Pub. No.: WO2019/073204
PCT Pub. Date: Apr. 18, 2019

(65) Prior Publication Data
US 2020/0282159 A1 Sep. 10, 2020

(30) Foreign Application Priority Data
Oct. 9, 2017 (GB) ...................................... 1716507

(51) Int. Cl.
*A61M 11/02* (2006.01)
*A24F 42/20* (2020.01)
(Continued)

(52) U.S. Cl.
CPC ............. *A61M 11/02* (2013.01); *A24F 42/20* (2020.01); *A24F 42/60* (2020.01);
(Continued)

(58) Field of Classification Search
CPC .............. A61M 11/02; A61M 15/0025; A61M 15/0093; A61M 15/06; A61M 2209/045; A24F 42/20; A24F 42/60; A24F 15/015
See application file for complete search history.

(56) References Cited

U.S. PATENT DOCUMENTS 1,923,650 A * 8/1933 Westerfield ........... A61M 15/08
128/203.24
2,194,983 A * 3/1940 Neff ........................ A24F 15/18
206/269
(Continued)

FOREIGN PATENT DOCUMENTS

| EP | 0414536 A2 | 2/1991 |
| GB | 2204799 A | 11/1988 |

(Continued)

OTHER PUBLICATIONS

Definition for the term "bung", google and oxford dictionary.*
(Continued)

*Primary Examiner* — Tu A Vo
(74) *Attorney, Agent, or Firm* — Patterson + Sheridan, LLP

(57) ABSTRACT

An inhaler with an inner housing with a pressurised reservoir of an inhalable composition. A breath operated valve is operable by a user inhaling on an inhaling end of the inhaler. A composition flow path extends from the breath operated valve to the inhaling end via which the composition is dispensed when the breath operated valve is opened. The breath operated valve is biased closed by a biasing member contacting the breath operated valve at one end. A bung in the inner housing is positioned in an opening in the inner housing to support the end of the biasing member opposite to the breath operated valve. A rigid outer housing surrounds the inner housing and supports the bung.

16 Claims, 11 Drawing Sheets

(51) Int. Cl.
*A24F 42/60* (2020.01)
*A61M 15/00* (2006.01)
*A61M 15/06* (2006.01)
*A24F 15/015* (2020.01)

(52) U.S. Cl.
CPC .... *A61M 15/0025* (2014.02); *A61M 15/0093* (2014.02); *A61M 15/06* (2013.01); *A24F 15/015* (2020.01); *A61M 2209/045* (2013.01)

(56) References Cited

U.S. PATENT DOCUMENTS

| | | | | |
|---|---|---|---|---|
| 2,836,288 | A * | 5/1958 | Atchison | A24F 15/18 220/849 |
| 5,299,565 | A * | 4/1994 | Brown | A61M 16/00 128/203.25 |
| 6,509,005 | B1 | 1/2003 | Peart et al. | |
| 2006/0135599 | A1 | 6/2006 | Symonds et al. | |
| 2008/0271732 | A1* | 11/2008 | Weaver | A61M 15/025 128/200.14 |
| 2009/0084379 | A1* | 4/2009 | Goeckner | A61M 15/0043 128/203.15 |
| 2010/0199984 | A1* | 8/2010 | Williams, III | A61M 11/007 128/200.23 |
| 2010/0229881 | A1* | 9/2010 | Hearn | A61M 15/0096 131/273 |
| 2010/0242975 | A1* | 9/2010 | Hearn | F17C 5/06 131/273 |
| 2011/0315152 | A1* | 12/2011 | Hearn | A24F 42/60 131/273 |
| 2012/0138052 | A1* | 6/2012 | Hearn | A24F 42/60 128/202.21 |
| 2012/0138054 | A1* | 6/2012 | Hearn | A61M 15/0091 128/203.12 |
| 2012/0003049 | A1 | 12/2012 | Todd | |
| 2013/0037042 | A1* | 2/2013 | Hearn | A61M 15/06 141/18 |
| 2013/0056012 | A1* | 3/2013 | Hearn | A24F 42/20 131/273 |
| 2013/0061861 | A1* | 3/2013 | Hearn | A24F 42/60 131/329 |
| 2013/0074841 | A1* | 3/2013 | Von Schuckmann | A61M 15/0025 128/203.15 |
| 2013/0174842 | A1* | 7/2013 | Young | A61L 9/032 128/203.14 |
| 2013/0256163 | A1* | 10/2013 | Cottle | B65D 50/04 206/265 |
| 2015/0217067 | A1* | 8/2015 | Hearn | A61M 15/06 128/203.15 |
| 2015/0231108 | A1* | 8/2015 | Hearn | A61K 9/008 128/200.14 |
| 2015/0297844 | A1* | 10/2015 | Hearn | A24F 42/20 128/200.14 |
| 2015/0374034 | A1* | 12/2015 | Hearn | A61K 31/465 131/273 |
| 2016/0050973 | A1* | 2/2016 | Hearn | A61M 15/0091 131/328 |
| 2016/0052700 | A1* | 2/2016 | Hearn | B65B 31/047 141/5 |
| 2016/0095355 | A1* | 4/2016 | Hearn | A24F 40/485 131/273 |
| 2016/0280450 | A1* | 9/2016 | Hearn | B65D 83/752 |
| 2016/0366946 | A1* | 12/2016 | Murison | B67D 7/02 |
| 2017/0043999 | A1* | 2/2017 | Murison | B67D 7/145 |
| 2017/0045150 | A1* | 2/2017 | Marsh | H02J 7/342 |
| 2017/0045994 | A1* | 2/2017 | Murison | A61M 15/06 |
| 2017/0048927 | A1* | 2/2017 | Murison | A24F 40/50 |
| 2017/0048930 | A1* | 2/2017 | Marsh | B65B 3/04 |
| 2017/0064997 | A1* | 3/2017 | Murison | A24F 40/53 |
| 2017/0094999 | A1 | 4/2017 | Hearn et al. | |
| 2017/0099878 | A1* | 4/2017 | Murison | A24F 15/015 |
| 2018/0104425 | A1* | 4/2018 | Hogwood | A61M 11/047 |

FOREIGN PATENT DOCUMENTS

| | | | |
|---|---|---|---|
| WO | 2002/064109 | A2 | 8/2002 |
| WO | 2003/055549 | A1 | 7/2003 |
| WO | 2004/000290 | A1 | 12/2003 |
| WO | 2005094400 | A2 | 10/2005 |
| WO | 2009/001078 | A2 | 12/2008 |
| WO | 2009/001082 | A1 | 12/2008 |
| WO | 2010/073018 | A1 | 7/2010 |
| WO | 2011/015825 | A1 | 2/2011 |
| WO | 2011/015826 | A1 | 2/2011 |
| WO | 2011/117580 | A2 | 9/2011 |
| WO | 2014/033438 | A1 | 3/2014 |
| WO | 2014/033439 | A1 | 3/2014 |
| WO | 2014/155089 | A1 | 10/2014 |
| WO | 2014/155090 | A1 | 10/2014 |
| WO | 2014/155091 | A1 | 10/2014 |
| WO | 2014/155092 | A1 | 10/2014 |
| WO | 2014/155093 | A1 | 10/2014 |
| WO | 2014/155095 | A2 | 10/2014 |
| WO | 2015/087045 | A1 | 6/2015 |
| WO | 2015121673 | A1 | 8/2015 |
| WO | 2016/005728 | A1 | 1/2016 |
| WO | 2016/046567 | A1 | 3/2016 |

OTHER PUBLICATIONS

Definition for the term "bung", merriam-webster.com.*
Definition for the term "latch", merriam-webster.com.*
International Search Report and Written Opinion dated Dec. 21, 2018 in related application PCT/GB2018/052830.
UK Search Report dated Mar. 14, 2018 in related application GB1716507.7.

* cited by examiner

INHALER PARTICULARLY A CANNABINOID INHALER AND A METHOD OF ASSEMBLING SUCH AN INHALER

The present invention relates to an inhaler particularly a cannabinoid inhaler and method of assembling such an inhaler.

Cannabinoids have long been known for their therapeutic potential in pain relief, treatment of seizures, antiemesis et cetera. It is, however, a class of compounds whose usage has been associated with a great deal of debate owing to its psychoactive effects. It was not until the discovery of cannabinoid receptors (CB1 and CB2) and the isolation of individual cannabinoids such as THC (tetrahydrocannabinol), CBD (cannabidiol), CBN (Cannabinol), and THCV (Tetrahydrocannabivarin), that the psychoactive effects could be attributed primarily to compounds (like THC) with high affinities to the receptor CB1. Furthermore, it has been established that individual cannabinoids differ from one another in their affinities to receptors and certain cannabinoids, such as CBD, behave as CB1/CB2 antagonists, thereby blocking some actions of their agonists, such as THC.

With on-going research, therapeutic applications of cannabinoids are becoming increasingly evident, resulting in legalisation of these compounds for medical purposes in a number of countries. The primary targets of research in this field are being associated with safe, rapid and/or effective delivery of cannabinoids.

A number of ways of delivering cannabinoids are known in the art.

For example, US2012/0304990 teaches the use of heating to vaporise a cannabis deposit. One drawback of this system is that there is only a small temperature differential between the temperature at which the cannabis will vaporise (180° c. to 200° c.) and the temperature at which toxins are produced (230° c.).

A number of documents (for example WO03/055549, U.S. Pat. No. 6,509,005 and WO2004/000290) disclose the use of a metered dose inhaler. Such inhalers suffer from a number of drawbacks. Firstly, the metering chamber is relatively small, generally less than 100 µl resulting in delivery of fairly concentrated doses. Also, such devices require users to optimally co-ordinate actuation of the outlet valve and inhalation, failing which, dose delivery could be variable.

A further common mechanism is the simple spray which is disclosed, for example, in WO02/064109 and US2006/135599 which are designed to provide a sublingual or buccal spray. Such a spray is currently being marketed by GW Pharmaceuticals under the Sativex (™) brand. These sprays suffer from the possibility of non-uniform drug dose delivery owing to the flushing action of saliva. Further, they have a slower onset of action when compared with pulmonary delivery.

A development of this idea was disclosed in WO2015/121673. This takes an inhaler which is based on a simulated cigarette and uses it to dispense cannabis.

The inhaler is based on a design of simulated cigarette which uses a pressurised reservoir and a breath operated valve. Suction on an inhaling end of the inhaler opens the breath operated valve such that the pressurised reservoir is able to dispense the formulation.

The inhaler is primarily designed as a simulated cigarette. Details of the breath operated valve are described in WO2009/001082, WO2010/073018, WO2011/015825, WO2011/015826, WO2014/033438, WO2014/033439, WO2014/155091 and WO2016/005728.

Additional details of the inhaler are provided in: WO2011/117580 and WO2014/155093

Details of the manner in which the inhaler is tested and assembled are provided in WO2015/087045, WO2014/155095 and WO2016/046567.

The inhaler is designed to be refillable via a refill pack which is designed to have the shape and size of a cigarette pack. Details of the refill pack are provided in: WO2009/001078, WO2014/155092, WO2014/155090 and WO2014/155089

WO2015/121673 provides details of the composition required to dispense a cannabinoid based product from such an inhaler.

The above mentioned references provide a full description of the inhaler internal workings and the composition.

The present invention provides modifications of such an inhaler which are suitable for dispensing a cannabinoid product.

One issue with the above described inhaler concerns the presence of a spring which is designed to bias closed the breath operated valve. This is inserted into the inhaler before a cap is put in place and welded in position. This is an awkward operation as the cap covers the spring rendering it inaccessible during this part of the assembly process. Further, the metal spring can heat up during the welding process such that the spring can embed itself in the surrounding materials and this will affect the biasing force with which it biases the valve closed.

According to the present invention, there is provided an inhaler according to certain claims.

The present invention uses an outer housing. This allows the support for the biasing member to be reconfigured to include a bung to support the biasing member rather than the welded cap as previously. The rigid outer housing then surrounds the inner housing to support the bung.

This modification is particularly applicable when the inhaler composition comprises a cannabinoid or a pharmaceutically acceptable derivative or salt thereof as the need for an outer housing is greater in such circumstances.

The inhaler preferably further comprises a membrane which is communication with an air flow path through the inhaler leading to the inhaling end, the membrane being configured to be deformable by the air in the air flow path to displace a valve element against the action of the biasing member. This membrane can provide a wide surface area which provides an optimal way of generating a relatively large force to overcome the biasing member in a relatively small space.

The inhaler preferably further comprises a cap which forms part of the inner housing adjacent to the biasing member, a hole being provided in the cap to receive the bung.

The outer housing can be formed of a number of components which are welded together. In this case, the welded joints can be kept further from the biasing member to avoid the problems with the welding heat set out above. However, preferably, the outer housing is formed of a number of components which are attached in a non-welded manner. Preferably the components are clipped together. In this case, they are preferably irreversibly clipped together such that the outer housing cannot be disassembled without permanently damaging the components.

This aspect of the present invention preferably also extends to a method of assembling the inhaler according to certain claims.

A problem with using the inhaler according to WO2015/121673 as a cannabis dispenser is that it is often used by those who have limited dexterity in their fingers. The inhaler of WO2015/121673 is designed to be held in the finger tips and pressed against the refill nozzle in order to refill the inhaler.

According to a second aspect of the present invention there is provided another inhaler according to certain claims.

By providing a much larger inhaler with a relatively flat body, it is much easier for those with a limited dexterity to refill it as it can be held more easily between the thumb, the index finger and palm of the hand.

In order to enhance this, the flattened shape comprises opposing flat surfaces, wherein at least one of the flat surface comprises a recess which extends for at least one third (preferably at least one half) of the length of the inhaler and at least one third (preferably at least one half) of the width of the inhaler. The edges of this relatively large recess provide additional surface which makes it easier for a user to manipulate the inhaler. In particular, the depth of the recesses is preferably greater than 10% of the depth of the inhaler. The relatively deep recess provides a surface towards the inhaling end of the inhaler against which a user can push when mating the device with the refill pack. Whilst there may only be a recess on one side of inhaler, preferably each of the flat surfaces comprises a respective recess.

In view of the nature of the composition being dispensed, the inhaler should be capable of being stored in a child-resistant manner. No such child-resistant storage is provided in WO2015/121673.

According to a third aspect of the present invention there is provided a combination of an inhaler and a refill pack according to certain claims.

By providing latches at each end of the housing, which are spaced at least 80 mm (preferably 90 mm) apart, the refill pack cannot readily be operated by accident by a child holding the refill pack in one hand as their hand will not be able to reach both latches at the same time. They can, of course, still open the container using both hands, but this requires a great deal more dexterity and coordination and is far less likely to happen accidently. At the same time, given that the refill is intended to be used by those with a limited dexterity, the fact that it can still be opened simply by depressing two latches at opposite ends of the housing provides a mechanism which is easy to use. The mechanism can also readily be accommodated in the refill pack without unduly affecting its aesthetics.

Also, in view of the nature of the composition, it is desirable that a user is not able to dispense the composition directly from the refill canister. This can be dealt within the refill canister itself by recessing the refill nozzle while inside the refill pack housing. In accordance with a fourth aspect of the present invention, there is provided a combination of a cannabinoid inhaler and a refill pack according to certain claims.

Because the only way to obtain access to the pressurised canister is to destroy the refill pack housing, this will deter any casual attempts to do this. Whilst it is still possible to destroy the housing, this is by no means straightforward and risk damaging the pressurised canister. As such, it is unlikely that this will be attempted by the casual user and therefore offers a greater degree of protection than WO2015/121673. The parts of the refill pack may, for example, be clipped together in an irreversible manner such that they cannot easily be separated and such that separating them will then inevitably result in permanently damaging the housing.

Preferably, however, the at least two parts are welded together, for example, by sonic welding.

According to a fifth aspect of the present invention there is provided another combination of a cannabinoid inhaler and refill pack according to certain claims. By making the refill pack housing have a curved cross section which is wider at the containing the pressurized canister, this provides ergonomic advantages. This shape naturally encourages the user to grip the refill pack housing at the wider end which is the end at which they will insert the inhaler in order to carry out the refill operation. Because they are holding this end, this provides a stable base from which to press the inhaler against the refill pack.

Preferably the housing is provided with a transparent window in the vicinity of an outlet from the pressurised refill canister. This allows the user to have a visual guide of the mating between the inhaler and the outlet from the pressurised refill canister.

Preferably the refill end of the inhaler is configured to fit closely into a recess in the vicinity of an outlet from the pressurised refill canister. This helps guide the inhaler into the refill position, potentially aided by the presence of the transparent window.

Examples of the various aspects of the present invention will now be described with reference to the accompanying drawings, in which.

Figure 6A:
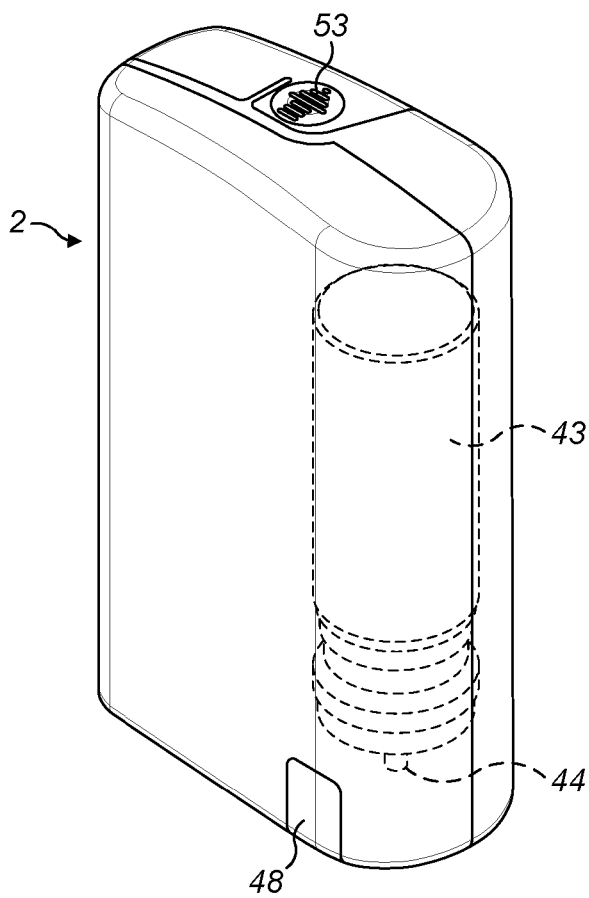
FIGS. 6A to 6D are top back perspective, top front perspective, bottom back perspective and bottom front perspective views respectively of the refill pack.
Figure 6B:
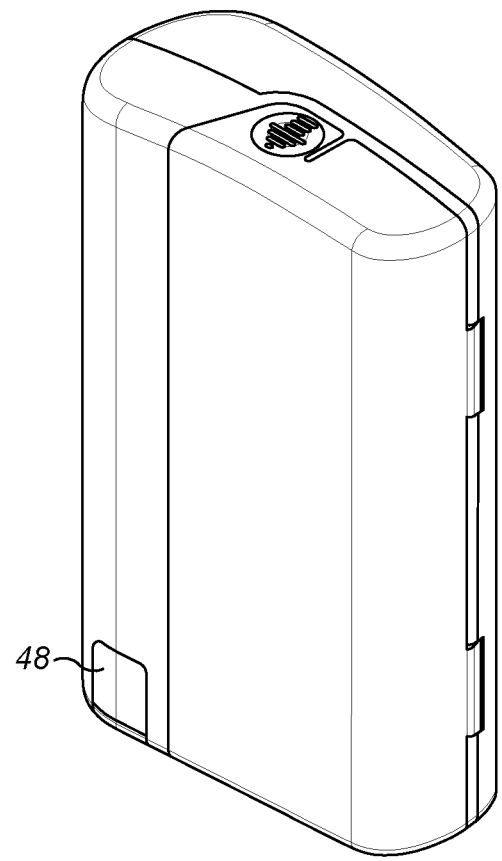
Figure 6C:
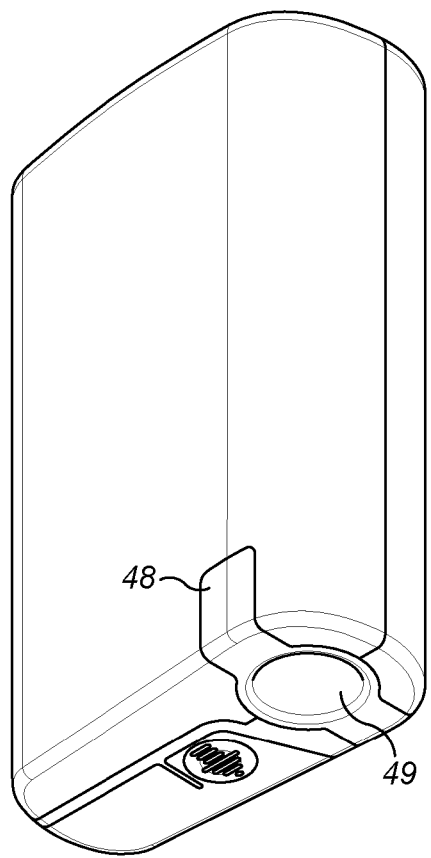
Figure 6D:
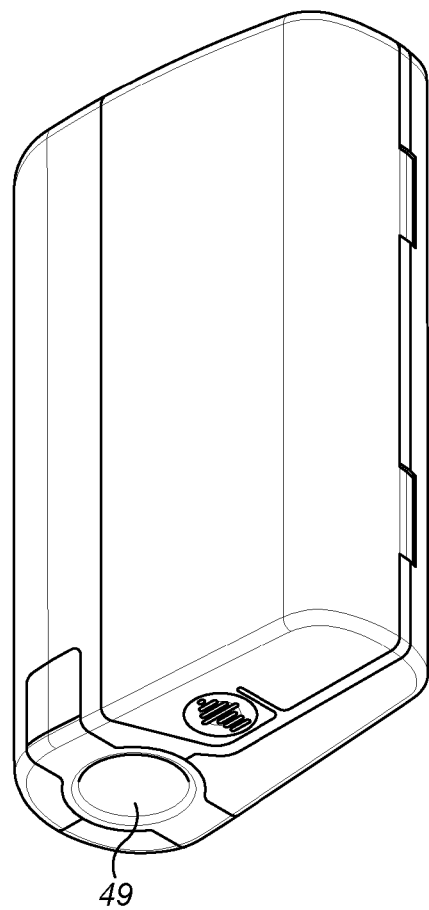
Figure 7A:
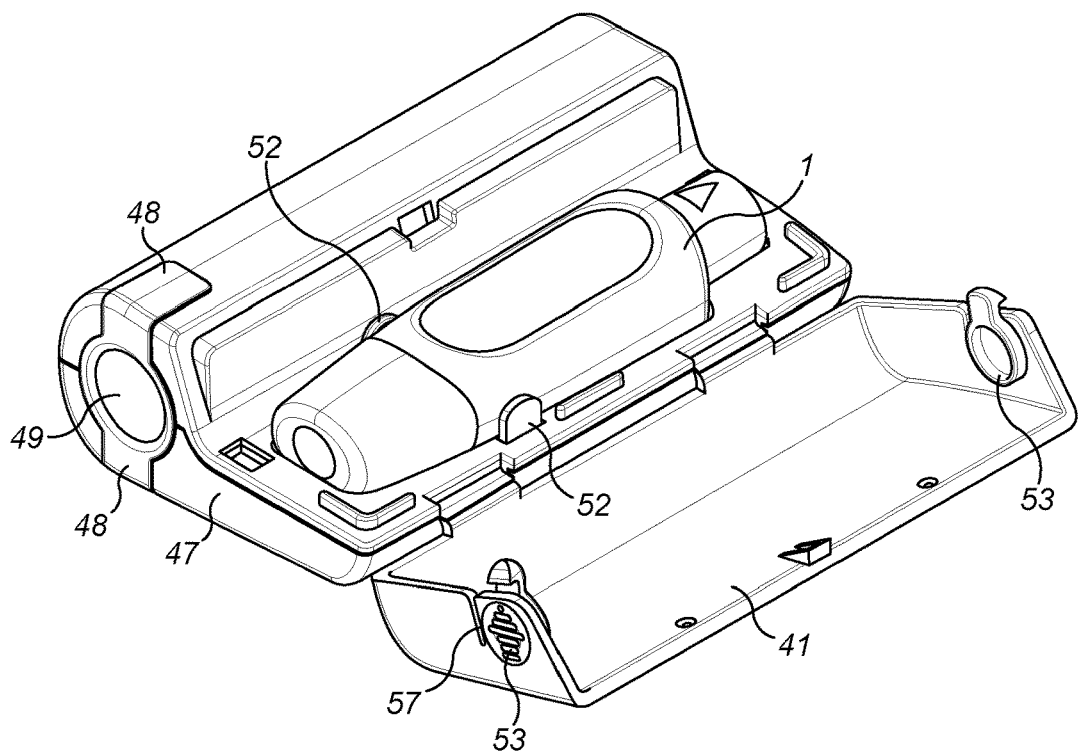
FIGS. 7A and 7B are perspective views of the refill with the door opened, with the inhaler shown in place in FIG. 7A and removed in FIG. 7B.

The present invention comprises an inhaler device 1 shown in FIGS. 1-4 and 7A and a refill pack 2 shown in FIGS. 5 to 7.

The internal workings of the inhaler device 1 are based on an inhaler I which is described in all of the PCT publications referred to above. This forms the inner core of the present invention. The modification provided by the present invention is, in broad terms, to surround this inner core I with an outer housing 3 as described below.

In general terms, the workings of the inhaler I have not been modified and this will therefore not be described in great detail here.

In broad terms, the inhaler core comprises a reservoir 4 and a breath operated valve mechanism 5 which has a spring loaded member valve member 6 (see FIG. 3B) which pinches a deformable tube 7 closed to close off access to the reservoir. The valve element 6 is biased closed by a spring 8. A membrane 9 is in communication with an air flow path such that suction on the outlet end 10 causes a change of pressure on the membrane which will lift the valve element 6 against the action of the spring 8. Further details of this are given in the above references.

The inhaler core also has a dip tube 11 which is held by a fixture 12 adjacent to a refill valve 13. This allows the inhaler I to be refilled at the refill end 14. Again, further details can be found in the above mentioned references.

Figure 3:
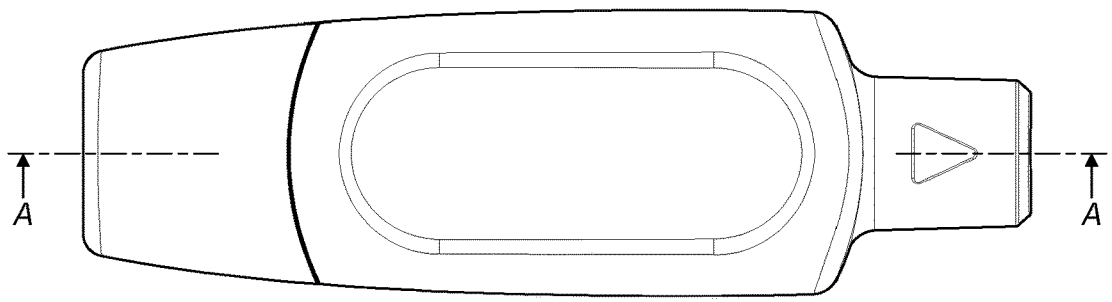
FIG. 3 is a top view of the inhaler.
Figure 3A:
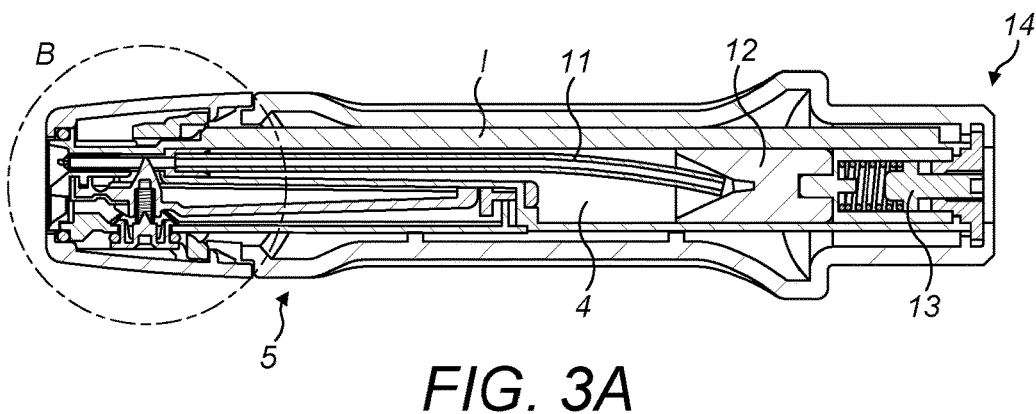
FIG. 3A is a cross section through line A-A in FIG. 3.
Figure 3B:
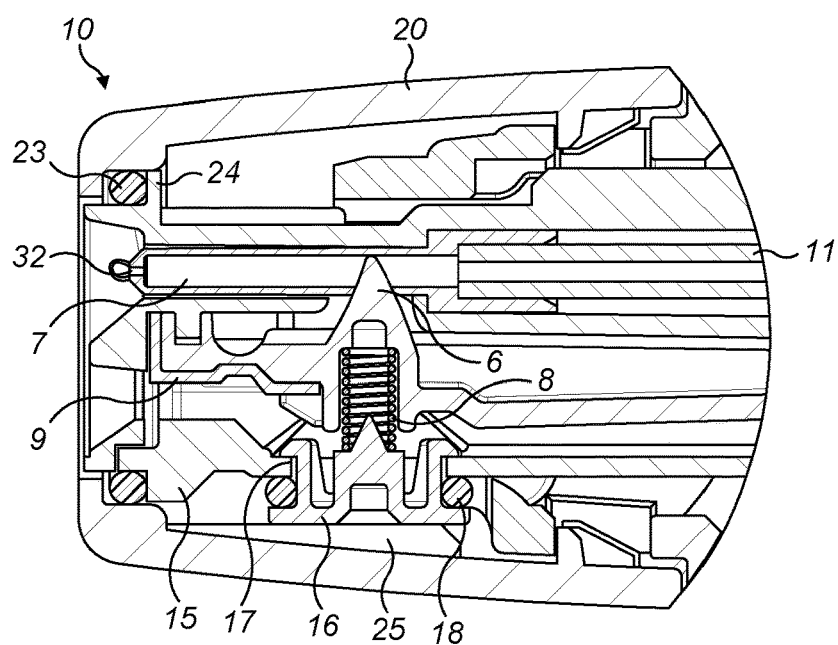
FIG. 3B is an enlarged cross section of the part within the ring B in FIG. 3A.
Figure 4A:
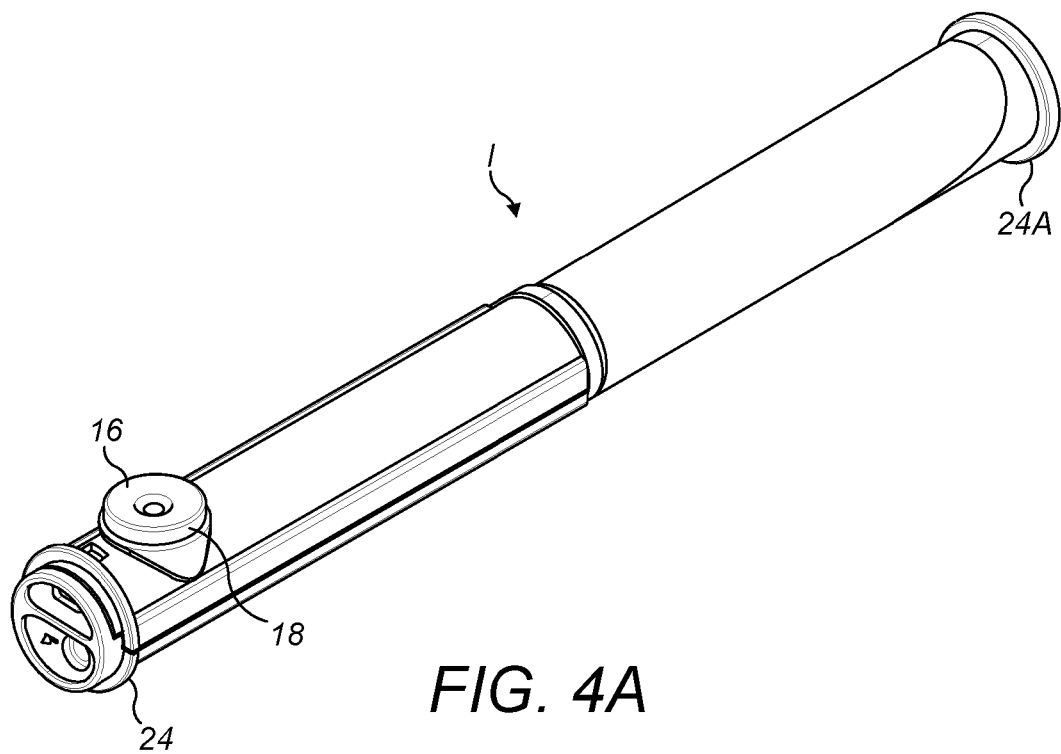
FIGS. 4A and 4B are a top perspective and bottom perspective view respectively of the internal core.
Figure 4B:
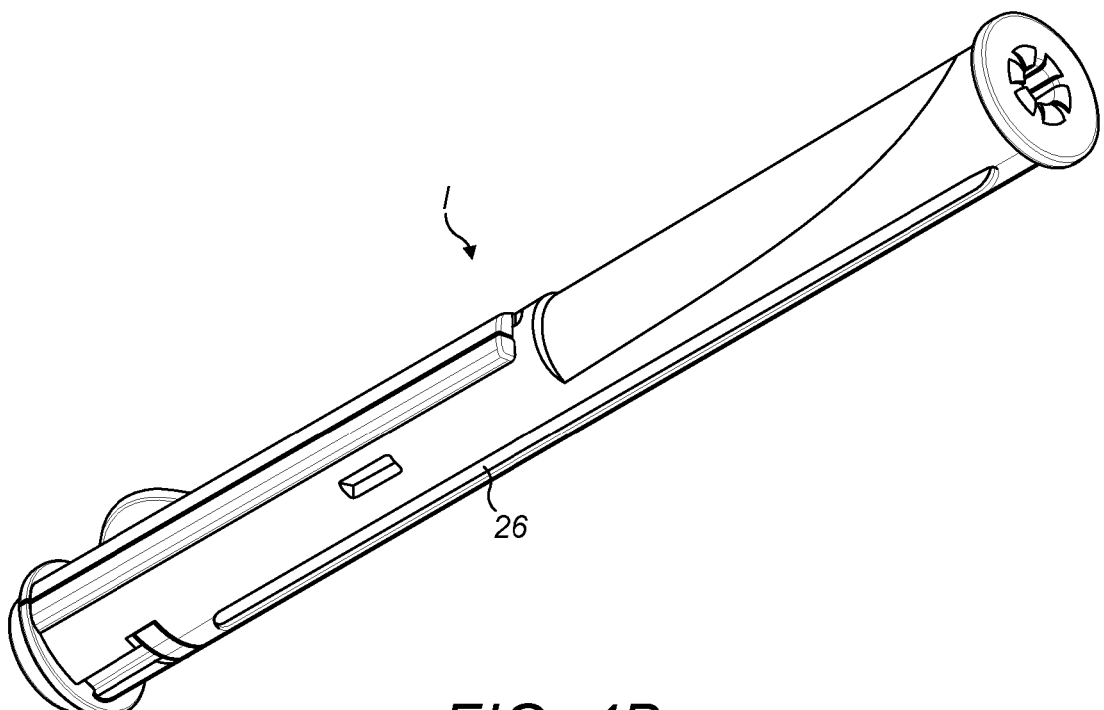

One modification to the inhaler I is illustrated in FIG. 3B. The inhaler I is closed in the vicinity of the membrane 9 by a cap 15 which in the above mentioned references directly support the spring 8. In the present case, however, a further component in the form of a bung 16 is inserted through an opening 17 in the cap and is sealed by an O ring 18. This allows the cap 15 to be welded in place before the spring 8 is put in place and then retained by the bung 16.

As is apparent, for example, from FIGS. 1 and 2, the outer housing 3 is made up of three separate portions, namely a mouthpiece casing 20, a top casing 21 and a bottom casing 22 which are clipped together to form the outer housing. As can be seen in FIG. 3B, an O-ring 23 seals a flange 24 on the inhaler core to the mouthpiece casing 20. This flange 24 represents a further modification of the inhaler I. A similar flange 24A is present at the opposite end to the outer housing 3. The mouthpiece casing 20 is also provided with a number of ribs 25 (only one of which is visible in FIG. 3B) to prevent the bung 16 from being dislodged.

The inhaler core I is also held in place within the outer housing 3 by the presence of an elongate rib 26 which extends along a significant portion of the length of the inhaler I and engages with a corresponding slot in the outer housing 3 to retain the inhaler I in place.

As shown particularly in FIGS. 1 and 2, the outer housing 3 is provided with a number of ergonomic features to enhance the usability of the inhaler device 1 particularly for those with limited manual dexterity.

Figure 1C:
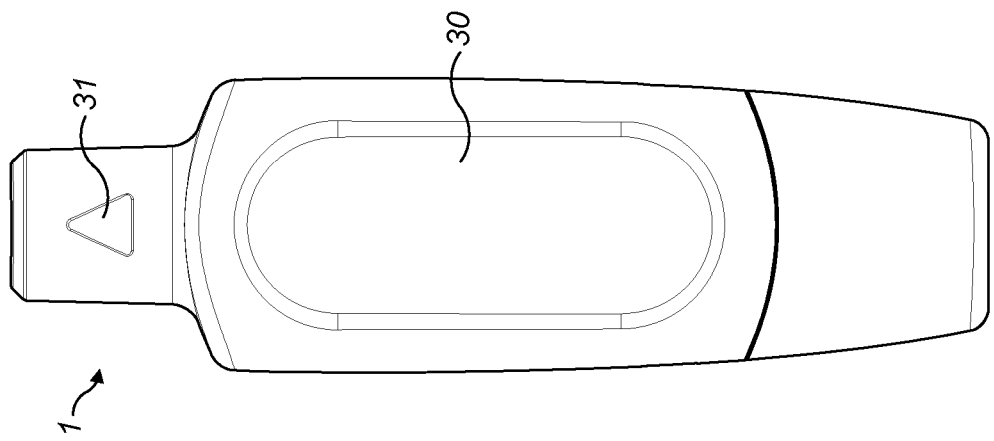
FIGS. 1A to 1F are a front, left, top, right, bottom and back views respectively of the inhaler.
Figure 1B:
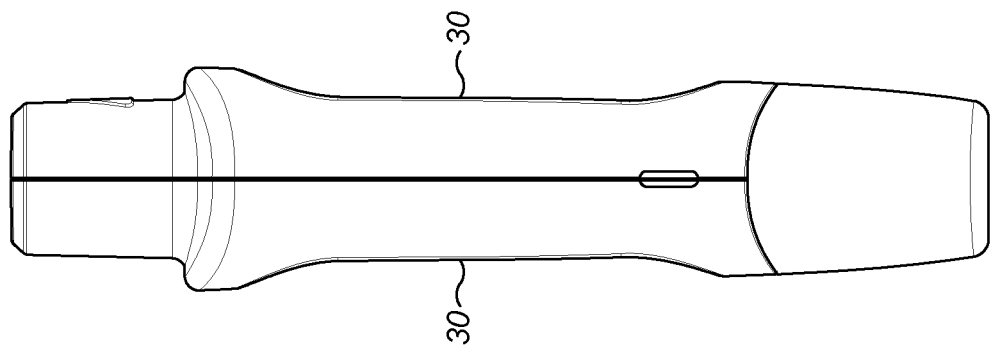
Figure 1A:
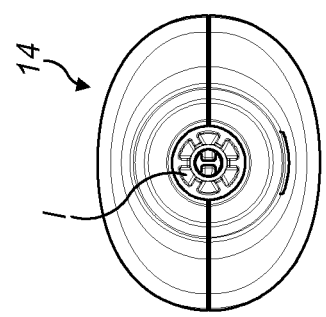
Figure 1F:
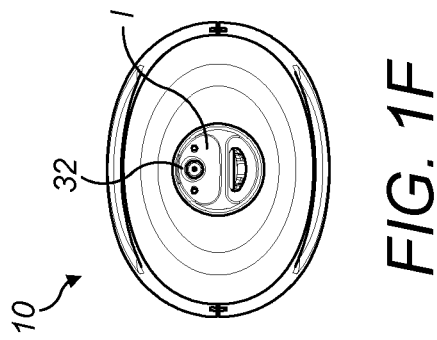
Figure 1E:
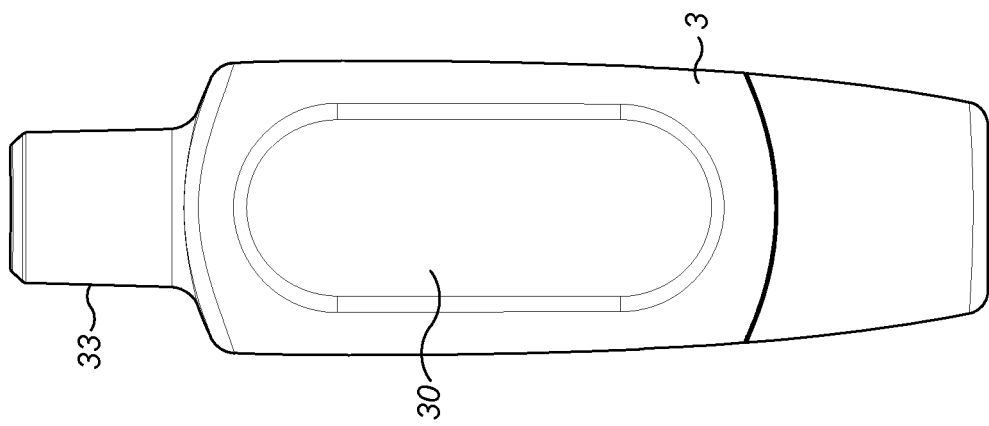
Figure 1D:
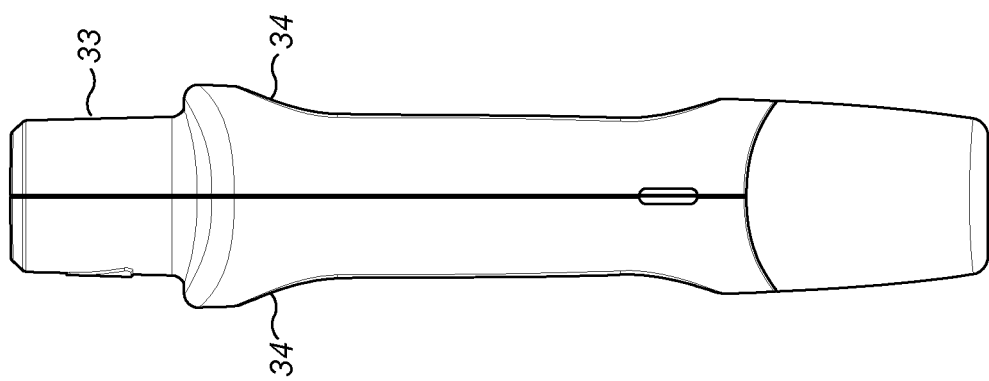
Figure 2A:
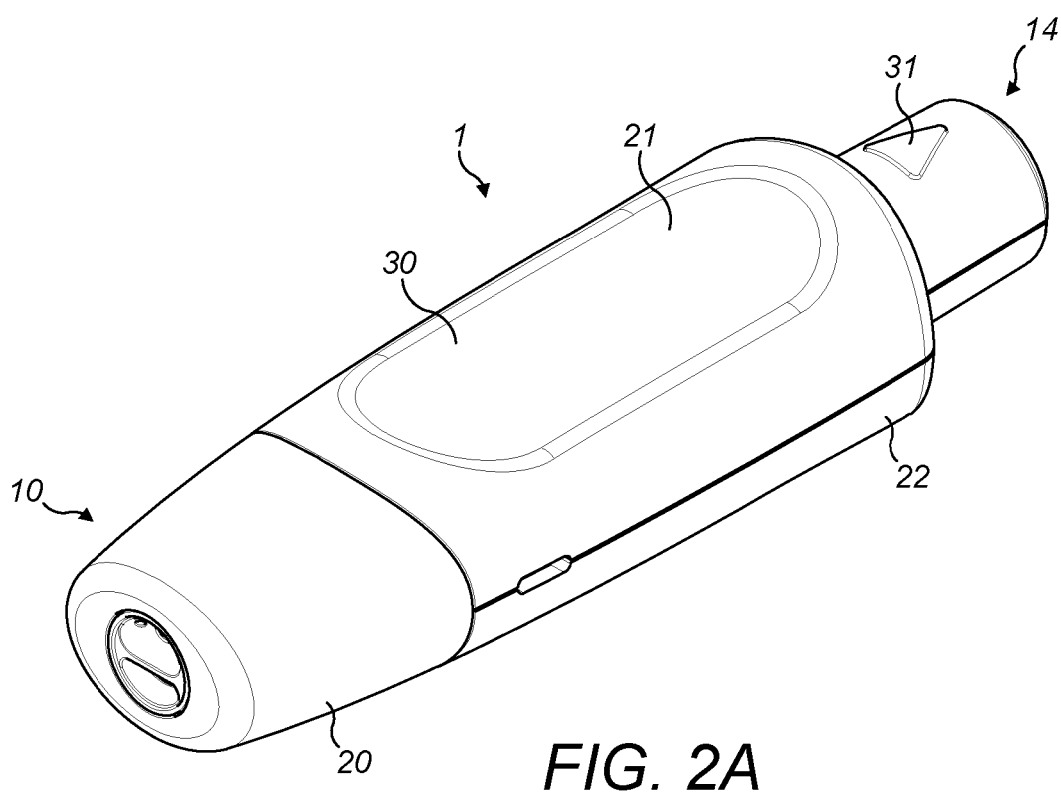
FIGS. 2A to 2D are a top back perspective, top front perspective, bottom back perspective and bottom front perspective views respectively of the inhaler.
Figure 2B:
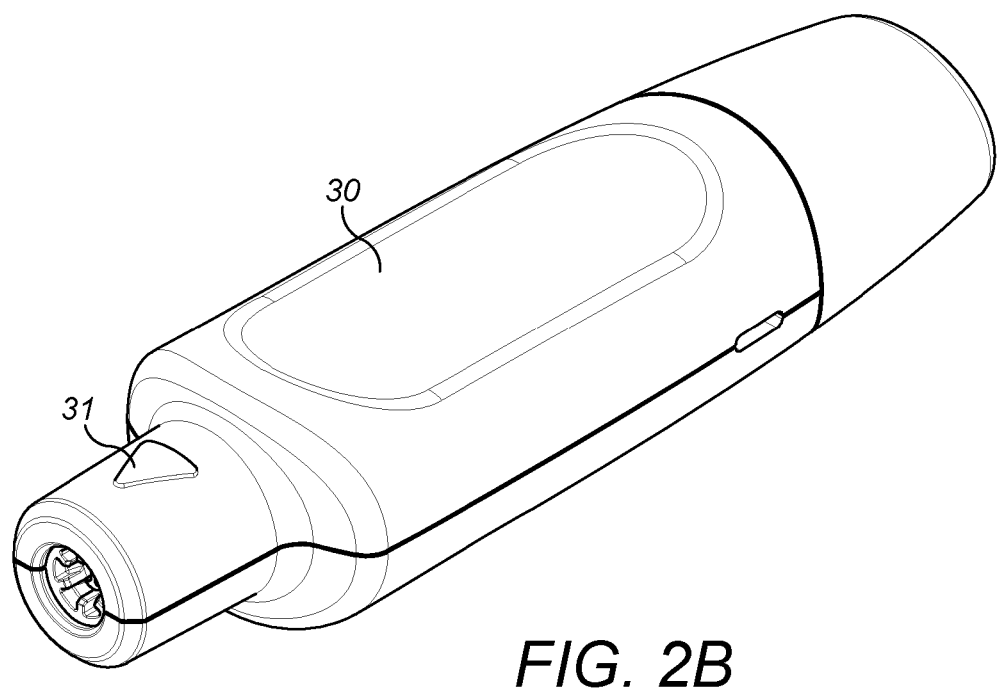
Figure 2C:
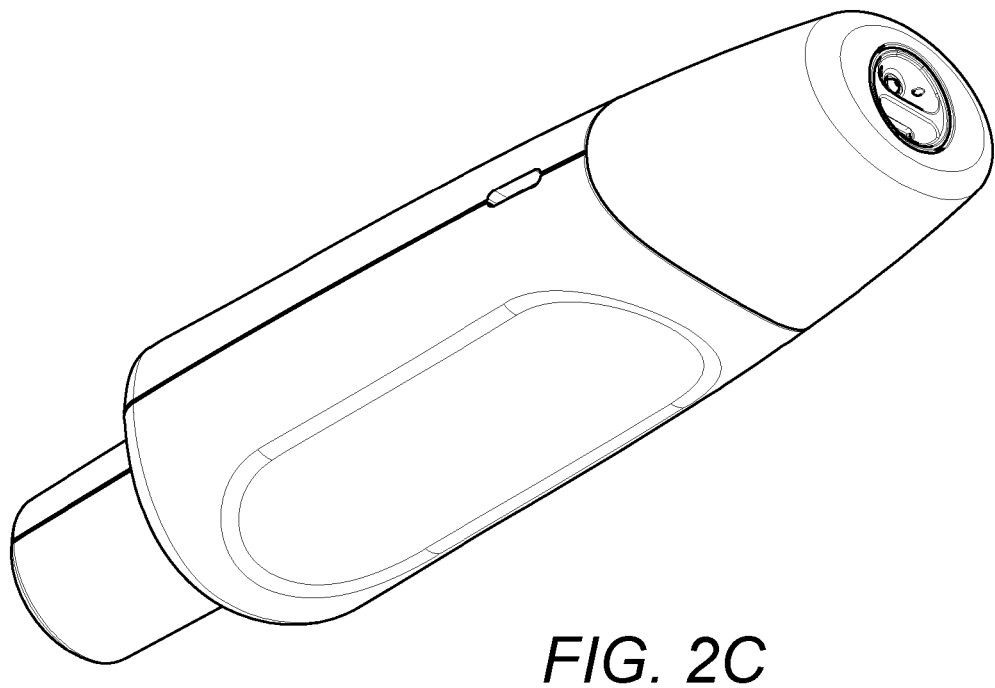
Figure 2D:
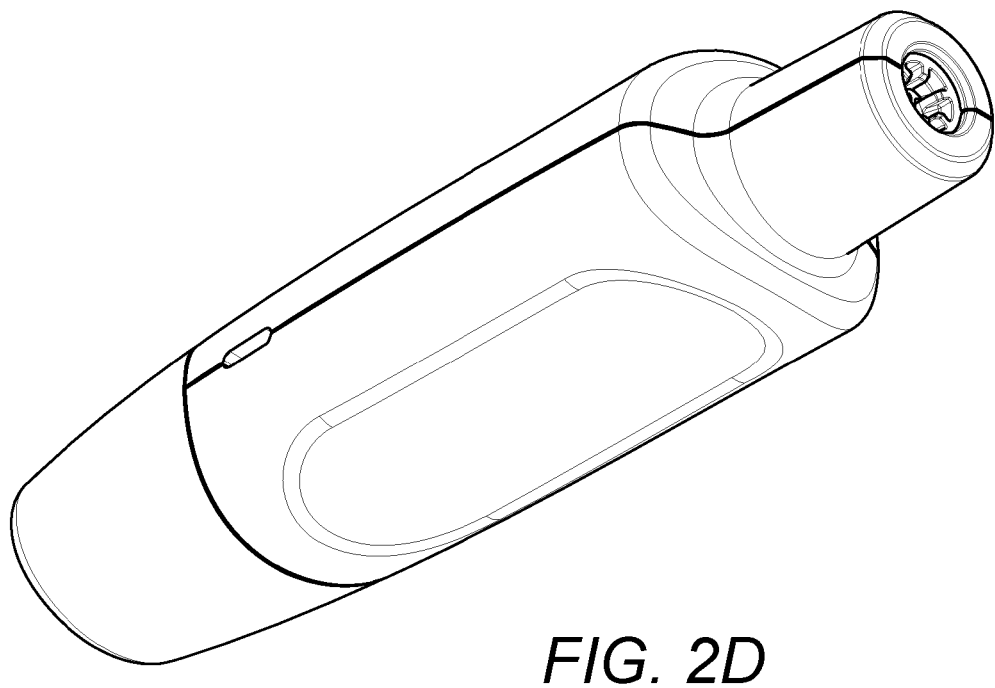

Thus, the outer housing 3 is provided with a significantly larger size than the inhaler core as can be seen, for example, from FIG. 3A as well as FIGS. 1A and 1F in which the inhaler I is visible at the inhaling 10 and refill 14 ends. The inhaler is approximately 26 mm across in its widest position and is preferably approximately 20 mm deep at its widest position. This provides the relatively flat elongate configuration apparent from FIGS. 1A and 1F. Recesses 30 are provided in the top and bottom surfaces of the outer housing 3 as seen in many of the figures. This makes the inhaler device 1 easier to grip both during the inhaling process and as it is refilled. During inhaling, the user will grip the inhaler by placing their fingers on the top recess and their thumb against the bottom recess. The inhaler can be used either way up, but it is provided with an indica in the form of an arrow 31 marking the top of the inhaler to encourage the inhaler always to be used in the same orientation with the arrow uppermost. In this orientation, the composition outlet 32 (see FIGS. 1F and 3B) is uppermost. This provides a more uniform dosage pattern, although the inhaler will still operate in any orientation.

When the inhaler device 1 needs to be refilled, the refill end 33 is inserted into the refill pack 2 as described below. The recesses 30 provide a pair of surfaces 34 that can readily be gripped by a user and which are oriented such that a user can readily exert a pushing force urging the refill end 33 into the refill pack as described below.

The refill pack 2 will now be described with reference to FIGS. 5 to 7.

Figure 7B:
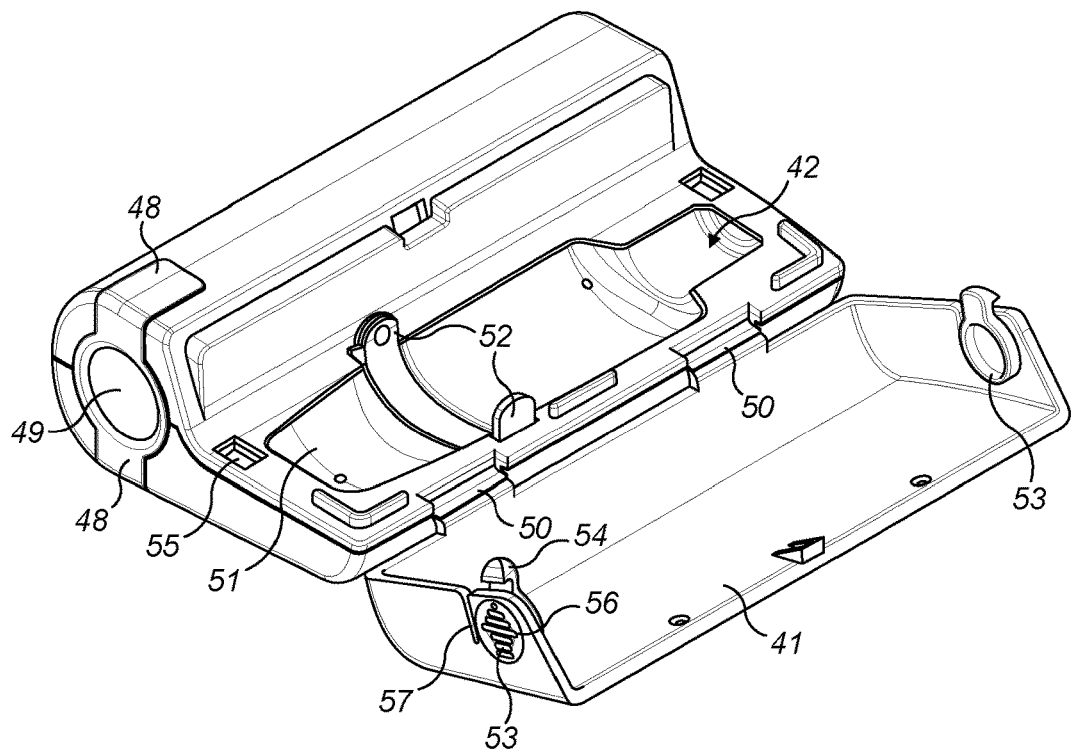

The refill pack 2 has a housing 40 with an openable door 41 as shown in FIGS. 7A and 7B, the refill pack 2 is essentially separated into two compartments namely a device storage compartment 42 located behind the door 41 and a compartment for the storage of a pressurised refill canister 43 depicted in FIG. 6A. This is a standard pressurised cylinder design and contains the composition defined in WO2015/121673. The canister 43 has a nozzle 44 which is depressed into the canister 43 by the inhaler device 1 in order to refill the inhaler device 1 as described in the above listed references directed to the refill pack.

The body of the housing 40 other than the door 41 is provided by two parts 45, 46 which are welded (eg. by sonic welding) along line 47 to encapsulate the canister 43. The canister 43 can therefore not be removed without destroying the housing 40. The parts can alternatively be clipped together in an irreversible manner.

A window 48 is provided in the housing 40 on both sides of the nozzle 44 so that a user can see when the refill end 33 of the inhaler device 1 is inserted into a recess 49 surrounding the nozzle 44. The recess 49 has a shape which is complimentary to the shape of the refill end 33 such that, not only can the user see the refill end being guided onto the refill nozzle 44, this is also guided by the interaction of the refill end 33 and the recess 49.

The door 41 is attached to the main body of the housing 40 by a pair of hinges 50 to allow the door 41 to be hinged between the closed position shown in FIGS. 5 and 6 and the open position shown in FIG. 7. As is apparent from FIG. 7B, the housing is provided with a recess 51 which is complimentary to the shape of inhaler device 1 in order to retain the inhaler device 1 in the place shown in FIG. 7A. A pair of clips 52 securely hold the retainer device 1 in place so that it does not fall out when the door 41 is opened but can then be easily removed.

A pair of latches 53 are provided one at each end of the door 41. Each comprises a hook 54 which is resiliently deformable to engage in a respective aperture 55 in the casing 40 and a release component 56 clearly marked with a visible arrow which has textured surface to allow the user to readily locate an engage with the release component 56. A notch 57 is provided in the door 40 in the vicinity of the release component 56 such that the release component 56 is deflectable inwardly of the housing to release the hook 54 from the aperture 55 thereby allowing the door to be opened. The latches 53 are deliberately positioned one at each end of the device, which has a length of approximately 100 mm such that they spaced apart by a distance which cannot be opened by a child holding the device in a single hand. They can, however, readily be opened by an adult sized hand.

Figure 5A:
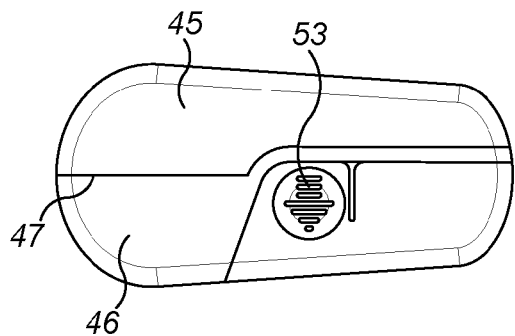
FIGS. 5A to 5F are top, back, left, front, right and bottom views respectively of the refill pack.
Figure 5B:
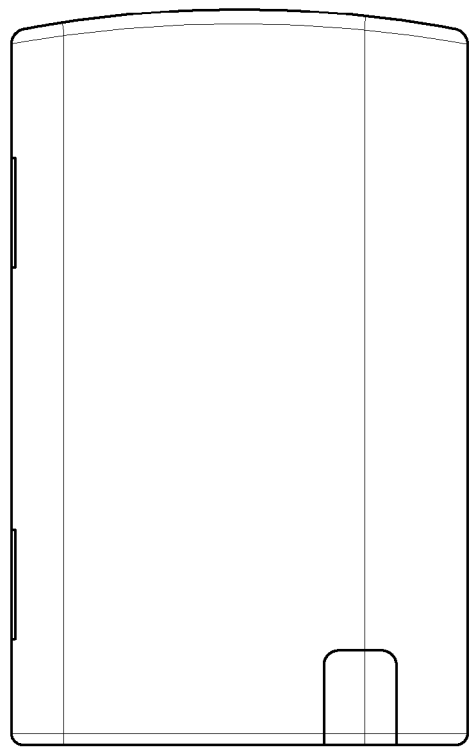
Figure 5C:
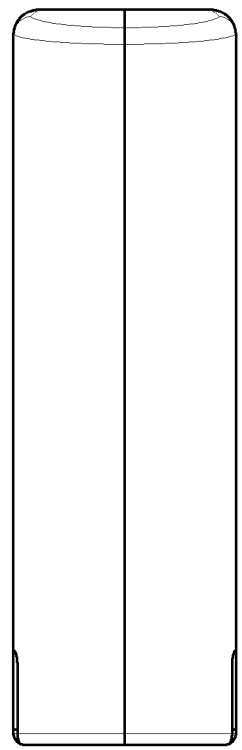
Figure 5D:
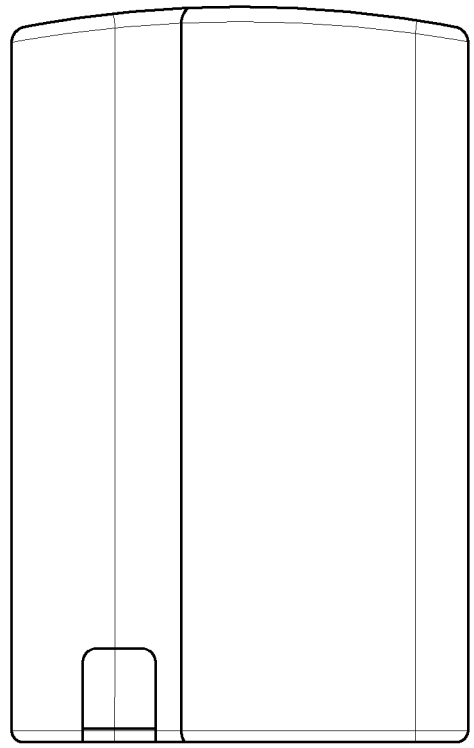
Figure 5E:
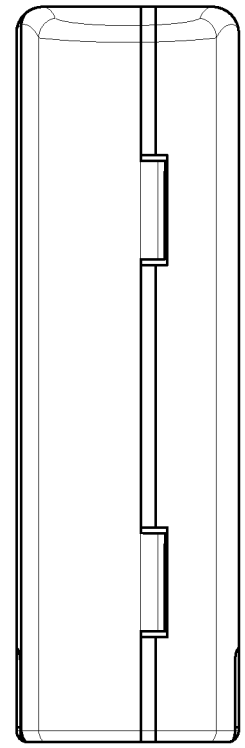
Figure 5F:
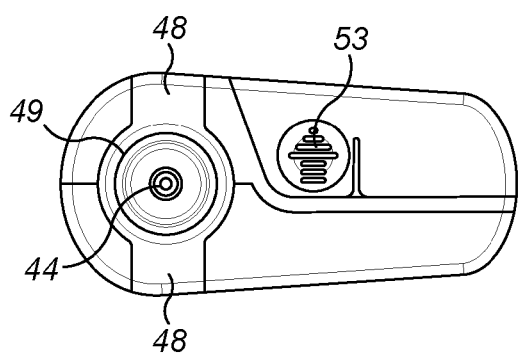

As will be apparent from FIGS. 5A and 5F, the housing 40 has a curved profile which is slightly wider at the end with the refill canister 43 than at the opposite end. This means that the user will naturally tend to grip the housing 40 around the wider end which provides a more stable arrangement as they insert the refill end 33 of the inhaler device 1 into the recess 49.

While certain claims specify a cannabinoid inhaler and require an inhalable composition comprising a cannabinoid, all aspects of the invention can be used with any inhalable pharmaceutical composition.

The invention claimed is:
1. An inhaler comprising:
an inner housing with a pressurised reservoir of an inhalable composition, the inner housing having an opening;
a breath operated valve operable by a user inhaling on an inhaling end of the inhaler;
a composition flow path from the breath operated valve to the inhaling end via which the composition is dispensed when the breath operated valve is opened;

the breath operated valve being biased closed at one end of the breath operated valve by a biasing member, a first end of the biasing member contacting the breath operated valve;

a bung extending through the opening in the inner housing, the bung being positioned in an opening in the inner housing to support a second end of the biasing member opposite to the first end of the biasing member that contacts the breath operated valve such that the biasing member extends between the breath operated valve at the first end of the biasing member and the bung at the second end of the biasing member;

and a rigid outer housing surrounding the inner housing and supporting the bung.

2. An inhaler according to claim 1, wherein the inhalable composition comprises a cannabinoid or a pharmaceutically acceptable derivative or salt thereof.

3. An inhaler according to claim 1, further comprising a membrane which is in communication with an air flow path through the inhaler leading to the inhaling end, the membrane being configured to be deformable by air in the air flow path to displace a valve element against an action of the biasing member.

4. An inhaler according to claim 1, further comprising a cap which forms part of the inner housing adjacent to the biasing member, a hole being provided in the cap to receive the bung.

5. A method of assembling an inhaler according to claim 4, the method comprising the steps of:

attaching the cap to a remainder of the inner housing;

inserting the biasing member through the hole in the cap; attaching the bung to the cap in order to secure the biasing member in place;

and assembling the outer housing to support the bung.

6. An inhaler according to claim 1, wherein the outer housing is formed of a number of components which are attached in a non-welded manner.

7. An inhaler according to claim 6, wherein the components are clipped together.

8. An inhaler according to claim 7, wherein the components are irreversibly clipped together.

9. A cannabinoid inhaler comprising:

an inner housing;

a pressurised reservoir within the inner housing containing an inhalable composition comprising a cannabinoid or pharmaceutically acceptable derivative or salt thereof, a composition flow path from the reservoir and out of a composition outlet at an inhaling end of the inner housing;

a non-metered breath operated outlet valve for controlling the flow of the inhalable composition through the composition flow path;

a refill valve through which the reservoir is configured to be refilled, the refill valve positioned at a refill end of the inner housing opposite to the inhaling end; and an outer housing extending from the inhaling end of the inner housing to the refill end of the inner housing and surrounding the inner housing, the outer housing comprising a first opening for leaving the inhaling end of the inner housing exposed and a second opening for leaving the refill end of the inner housing exposed;

the outer housing of the inhaler having a main axis defining a longitudinal direction and in at least one cross section in a plane perpendicular to the longitudinal axis, a continuously curved flattened shape with a width to depth aspect ratio of greater than 1.2:1 and a maximum width of greater than 20 mm.

10. An inhaler according to claim 9 wherein the flattened shape comprising opposing flat surfaces, wherein at least one of the flat surfaces comprises a recess which extends for at least one third of a length of the inhaler and at least one third of a width of the inhaler.

11. An inhaler according to claim 10, wherein the recess extends for at least half of a length of the reservoir.

12. An inhaler according to claim 10, wherein the recess extends for at least half of the width of the inhaler.

13. An inhaler according to claim 10, wherein a depth of the recess is greater than 10% of a depth of the inhaler.

14. An inhaler according to claim 10, wherein each of the flat surfaces comprise a respective recess.

15. The combination of a cannabinoid inhaler and a refill pack;

the cannabinoid inhaler comprising a housing;

a pressurised reservoir within the housing containing an inhalable composition comprising a cannabinoid or pharmaceutically acceptable derivative or salt thereof, a composition flow path from the reservoir and out of a composition outlet at n inhaling end of the housing;

a non-metered breath operated outlet valve for controlling the flow of the inhalable composition through the composition flow path;

a refill valve through which the reservoir is configured to be refilled;

the refill pack comprising a housing having a recess to retain the inhaler, a pressurised canister of an inhalable composition, and a closable door to enclose the inhaler;

wherein the door is held closed by a first latch at a first end of the housing and a second latch at a second end of the housing, wherein each of the first and second latches being separately and independently operable by depressing a portion of the housing adjacent to the respective latch inwardly into the housing, the first and second latches being at least 80 mm apart.

16. A combination according to claim 15 wherein the latches are at least 90 mm apart.

* * * * *